United States Patent [19]

Rambert et al.

[11] Patent Number: 4,462,120

[45] Date of Patent: Jul. 31, 1984

[54] TOTAL KNEE PROSTHESIS

[76] Inventors: André Rambert, Les Fontanelles, 10 bis rue Dr. Bonhomme, 69003 Lyon; Gilles Bousquet, Chemin de Marandon, Saint-Etienne (Loire), both of France

[21] Appl. No.: 394,508

[22] Filed: Jul. 2, 1982

[30] Foreign Application Priority Data

Jul. 6, 1981 [FR] France ................................ 81 13723

[51] Int. Cl.³ ............................................. A61F 1/04
[52] U.S. Cl. .................................... 3/1.911; 128/92 C
[58] Field of Search ................ 3/1.9, 1.91, 1.94, 1.912, 3/1.913; 128/92 C, 92 CA

[56] References Cited

U.S. PATENT DOCUMENTS

| | | | |
|---|---|---|---|
| 3,696,446 | 10/1972 | Bousquet et al. | 128/92 C |
| 3,837,009 | 9/1974 | Walker | 3/1.911 |
| 3,848,276 | 11/1974 | Martinez | 3/1.911 |
| 4,073,999 | 2/1978 | Bryan et al. | 3/1.9 X |
| 4,178,641 | 12/1979 | Grundei et al. | 3/1.911 |
| 4,262,368 | 4/1981 | Lacey | 3/1.911 |

FOREIGN PATENT DOCUMENTS 2244064 3/1974 Fed. Rep. of Germany ....... 3/1.911

Primary Examiner—Richard J. Apley
Assistant Examiner—David J. Isabella
Attorney, Agent, or Firm—Karl F. Ross; Herbert Dubno

[57] ABSTRACT

A total knee prosthesis comprises an upper and a lower support member provided with externally threaded, tapered shanks to which they are detachably secured, these shanks being respectively screwable into the medullary canals of a femur and a tibia of a patient to be fitted with the prosthesis. The upper support member has spherically convex rear condylar extensions coming to rest on respective pads of the lower support member which are of different height determining the physiological valgus of the patient's leg. The condylar extensions are interconnected by an axle pin received in a bifurcate projection of the lower support member; a forward extension of the upper support member forms a concave shield engageble with the natural kneecap or with a prosthetic patellar disk of the patient.

10 Claims, 4 Drawing Figures

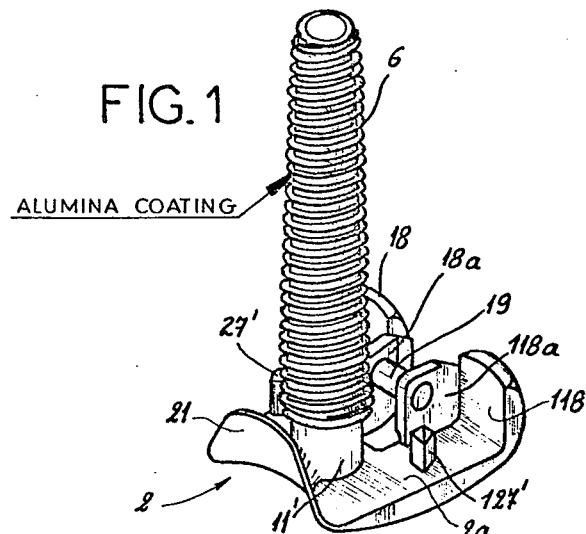
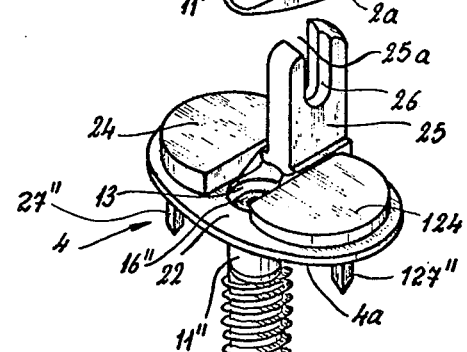
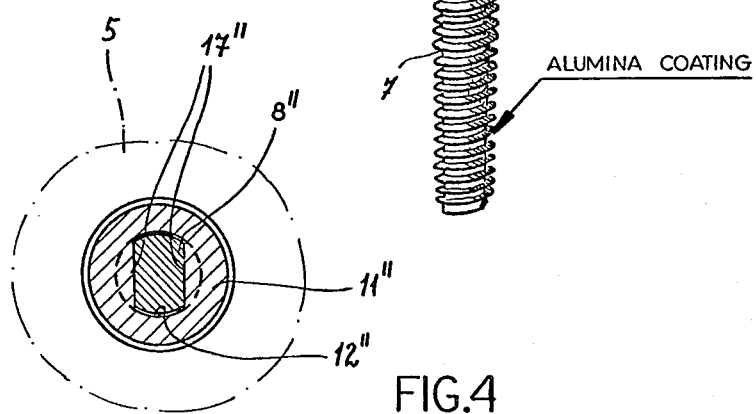

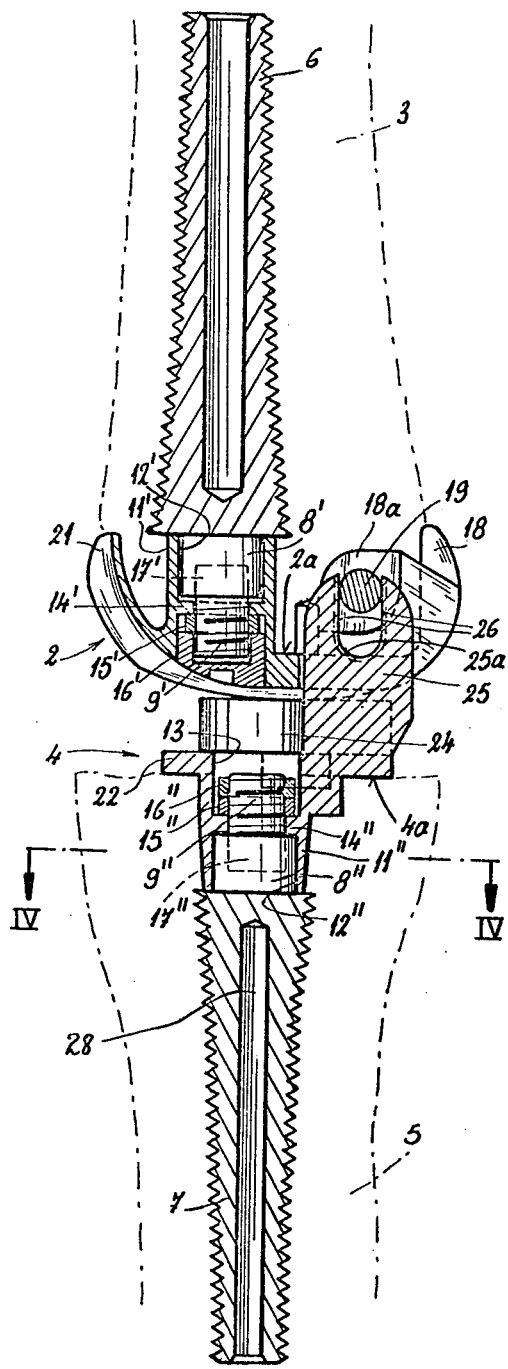
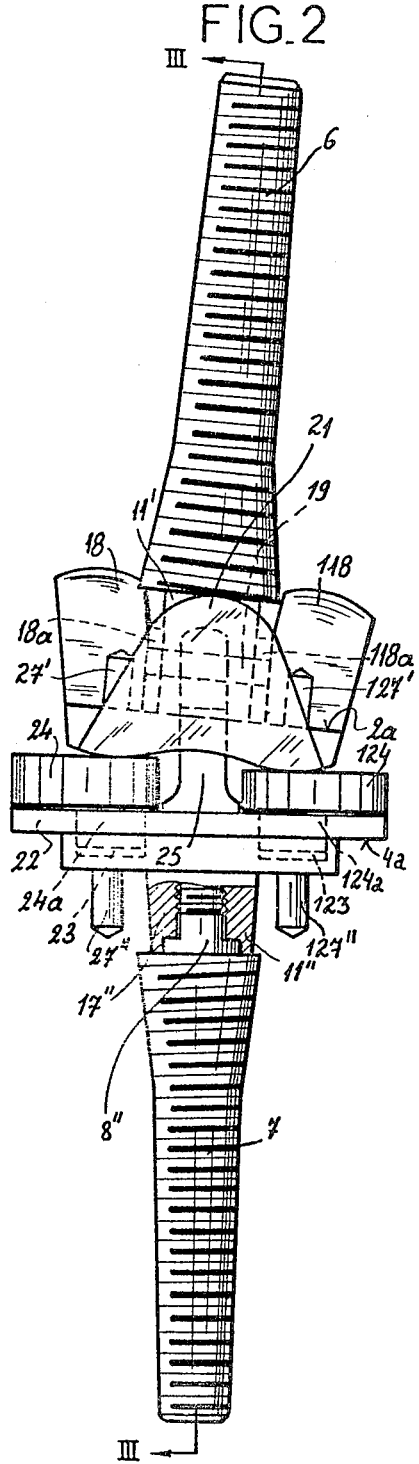
FIG. 3
FIG. 2

TOTAL KNEE PROSTHESIS

FIELD OF THE INVENTION

Our present invention relates to a total knee prosthesis designed to restore parts of the femur and tibia including the two condyles.

BACKGROUND OF THE INVENTION

Prostheses of this type are conventionally made with or without central stems. The presence of such a stem, which generally is cemented to the bone, affords greater stability but does not by itself prevent buckling in a plane perpendicular to the swing axis of the jacket; its insertion, furthermore, often necessitates the resection of much healthy bone tissue. Many of the existing prostheses, moreover, require extensive surgical operations when a worn part is to be replaced.

OBJECT OF THE INVENTION

The object of our present invention, therefore, is to provide an improved prosthesis for a knee joint which is stable without any cementing, is comfortable to the user and enables the replacement of worn parts in a relatively simple manner.

SUMMARY OF THE INVENTION

We realize this object, in accordance with our present invention, by providing an upper and a lower support member each having a tapering and externally threaded shank which is screwable into a medullary canal of a patient's femur and tibia, respectively. The femoral and tibial shanks are detachably secured by first and second fastening means to the corresponding support members which in turn have contact surfaces positioned for rolling interengagement upon the anchoring of the shanks to the respective bones.

According to a more particular feature of our invention, the contact surface of the upper support member is formed in part by a pair of rearwardly driving condylar prongs with convex rear and bottom faces while the contact surface of the lower support member is essentially formed by two pads respectively overlain by the prongs. These pads are preferably of different height to establish a relative inclination of the shanks by an angle representing the physiological valgus of the patient.

A further advantageous feature of our invention resides in the provision of a pin bridging the gap which separates the two prongs on the upper support member, this pin engaging in an upwardly open slot of a projection on the lower support member. The slot may be bounded by beveled front and rear edges also enabling a limited relative horizontal twisting of the two support members. A forward part of the upper support member is advantageously designed as an upwardly sloping concave shield which preferably merges into the two prongs and confronts the location of the patient's patella so as to be engageable either with the natural kneecap or with a prosthetic patellar disk if the kneecap has been removed.

BRIEF DESCRIPTION OF THE DRAWING

The above and other features of our invention will now be described in detail with reference to the accompanying drawing in which:

FIG. 1 is a perspective view of a knee prosthesis according to our invention, shown with its upper and lower support members separated from each other;

FIG. 2 is an elevational front view of the prosthesis of FIG. 1 in an assembled position;

FIG. 3 is a sectional elevational view of the prosthesis taken on the line III—III of FIG. 2; and FIG. 4 is a cross-sectional view taken on the line IV—IV of FIG. 3.

SPECIFIC DESCRIPTION

As shown in the drawing, our improved knee prosthesis comprises an upper support member 2 and a lower support member 4 in the form of generally horizontal plates. Upper support member 2 is detachably secured, in a manner more fully described hereinafter, to a tapering and externally threaded shank 6 adapted to be screwed into the medually canal of the femur 3 of a patient. In a similar manner, lower support member 4 is detachably secured to a tapering and externally threaded shank 7 which can be screwed into the medullary canal of the patient's tibia 5. The support members and their shanks preferably consist of a nonoxidizable metallic material such as stainless steel. We also prefer to coat the shanks 6 and 7 with an adhesion-promoting compound, such as alumina, favoring the calcification of spongy bone substance.

Shanks 6 and 7 are provided with respective necks 8' and 8" having threaded extremities 9' and 9" of reduced diameter which pass through transverse partitions 14', 14" of sockets 11' and 11" that are respectively integral with members 2 and 4. Necks 8' and 8" are received with a low-friction fit in outer wells 12' and 12" of sockets 11' and 11", bounded by the partitions 14' and 14", while the extremities 9' and 9" thereof extend into inner recesses of these sockets (designated 13 for socket 11") for engagement by nuts 15', 15" and counternuts 16', 16". Counternut 16' is designed as a slotted crown. Wells 12' and 12" are of noncircular cross-section for positive rotational coupling with the associated shanks in order to facilitate their threading into the medullary canals of the respective bones by the surgeon. Thus, as best illustrated for the upper support member 2 in FIG. 4, these wells have flat sides engaging correspondig flats 17', 17" on the associated necks 8' and 8". The final fastening of support members 2 and 4 to the respective shanks by nuts 15', 16' and 15", 16" need therefore not take place until after the shanks have been properly positioned and inspected by the surgeon. Obviously, the removal of these nuts to replace either or both of the support members—e.g. upon excessive wear of their contact surfaces—requires only minor surgical intervention. Members 2 and 4 have surfaces 2a and 4a which, in their attached position, come to rest on the resected bones 3 and 5.

The aforementioned contact surfaces are formed in the case of upper member 2 by a pair of rearwardly diverging prongs 18, 118 which have spherically convex bottom and rear faces and are formed with upstanding cheeks 18a, 118a bracketing the intervening gap. These cheeks 18a and 118a are bridged by a horizontal pin 19 which engages in a vertical slot 25a of a bifercate lug 25 rising from a platform 22 which is integral with socket 11" of member 4. Slot 25a is bounded by beveled front and rear edges 26 facilitating a certain relative horizontal twisting of members 2 and 4. It will also be noted that lug 25, pivoting about pin 19, cannot rotate clockwise beyond the position of FIG. 3 so that tibia 5 cannot swing forward relative to femur 3.

Prongs 18, 118 are integral with a forwardly extending and upwardly sloping concave shield 21 which is designed to abut the nonillustrated kneecap of the patient or, possibly, a prosthetic patellar disk replacing same. The convex undersides of prongs 18 and 118 are in rolling contact with a pair of pads 24, 124 carried on platform 22 of lower member 4, these pads having bosses 24a, 124a received in recesses 23, 123 of member 2. The two pads, which are in the form of part-circular disks, closely adjoin the base of lug 25 while leaving the recess 13 of socket 11" accessible for retightening or possible removal of nuts 15" and 16". Pad 24 is higher than its mate 124 so as to impart a certain inclination to the axis of shank 6, relative to that of shank 7, as seen in FIG. 2 (the illustrated prosthesis being assumed to be for the patient's right leg); this inclination corresponds to the physiological valgus of the patient. The pads are preferably made of a nonmetallic, wear-resistant material having a relatively low coefficient of friction, such as high-density polyethylene. If necessary, they can be replaced without detachment of member 4 from shank 7.

As clearly seen in the drawing, the slot 25a is straight and perpendicular to the contact surfaces of pads 24, 124, i.e. parallel to the axis of shank 7 and in a transverse midplane which contains that axis and bisects the platform 22. It will also be apparent that the slot is disposed close to the rear edges of pads 24, 124 and is thus set back from the line along which the convex underside of member 2 engages these contact surfaces in the stretched position of FIG. 3 in which the two shanks are approximately alligned with each other. From FIG. 3 it can also be seen that the pin 19 passes through the center of curvature of the spherically convex surface portions of prongs 18, 118 thereby facilitating a counterclockwise swinging of the tibia 5 relatively to the femur 3 corresponding to the normal bending of the patient's leg at the knee.

As also shown in the drawing, the two support members 2 and 4 are advantageously provided with respective pegs 27', 127' and 27", 127" disposed generally parallel to their shanks, with a height somewhat less than that of sockets 11' and 11", which penetrate into the bones for more securely fastening the support members thereto. Despite the presence of these pegs, therefore, members 2 and 4 can still serve as handles for screwing the shanks 6 and 7 into the respective bones, except in a final stage in which a socket wrench fitting their respective necks 8' and 8" may have to be used for this purpose.

It will thus be seen that our improved prosthesis gives the wearer virtually the same mobility as a natural leg while being stabilized against buckling or excessive twisting. The shanks 6 and 7, securely anchored to and embedded in the bones, can remain in place even if a replacement of one or the other support member 2, 4 should become necessary.

We claim:
1. In a knee prosthesis comprising a lower support member with a platform bisected by a transverse midplane, said platform being provided with two lower contact surfaces on opposite sides of said midplane, an upper support member having a pair of rearwardly diverging condylar prongs with undersides merging forwardly into a pair of downwardly convex upper contact surfaces positioned to roll on said lower contact surfaces, a lug rising from said platform in said midplane and projecting between said upper contact surfaces, a transverse pin on said upper support member received in a slot of said lug, a first shank rising from said upper support member for insertion into the medullary canal of a patient's femur, and a second shank descending from said lower support member with an axis in said midplane for insertion into the medullary canal of the patient's tibia, the improvement wherein said first and second shanks are externally threaded and are respectively provided with first and second fastening means for detachably securing same to said upper and lower support members, said first fastening means lying forwardly of said prongs, said lug being disposed rearwardly of said second fastening means with a beveled slot, enabling limited relative horizontal twisting of said support members, extending parallel to the axis of said second shank at a location set back from a line of engagement of said upper contact surfaces with said lower contact surfaces in a position of approximate alignment of said shanks with each other.

2. A knee prothesis as defined in claim 1 wherein said prongs have upstanding cheeks interconnected by said pin, said slot being upwardly open for enabling insertion of said pin into same from above.

3. A knee prosthesis as defined in claim 1 or 2 wherein said prongs have spherically convex bottom and rear faces, said pin passing through the center of curvature of said faces.

4. A knee prosthesis as defined in claim 1 or 2 wherein said lower contact surfaces are formed by pads of different height on said platform establishing a relative inclination of said shanks by an angle representing a physiological valgus.

5. A knee prosthesis as defined in claim 4 wherein said prongs consist of stainless steel and said pads consist of high-density polyethylene.

6. A knee prosthesis as defined in claim 1 or 2 wherein said upper support member forms forwardly of said first shank an upwardly sloping concave shield confronting the location of the patient's patella.

7. A knee prosthesis as defined in claim 1 or 2 wherein each of said shanks is integral with a threaded neck projecting toward the respective support member and forming part of the respective fastening means, said support members being provided with sockets surrounding the respective necks and having internal annular shoulders engaged by countersunk nuts screwed onto the free ends of said necks.

8. A knee prosthesis as defined in claim 7 wherein said necks and said sockets are of noncircular cross-section on the sides of said shoulders remote from said nuts for enabling positive rotational entrainment of said shanks by said support members.

9. A knee prosthesis as defined in claim 1 or 2 wherein said shanks are coated with a compound promoting the calcification of spongy bone substance.

10. A knee prosthesis as defined in claim 1 or 2 wherein each of said support members is provided with at least one peg extending generally parallel to the respective shank in a direction away from the other support member.

* * * * *